United States Patent
Klehn et al.

(10) Patent No.: US 7,174,212 B1
(45) Date of Patent: Feb. 6, 2007

(54) IMPLANTABLE MEDICAL DEVICE HAVING A CASING PROVIDING HIGH-SPEED TELEMETRY

(75) Inventors: Russell Klehn, Valencia, CA (US); Sergey Safarevich, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 445 days.

(21) Appl. No.: 10/733,654

(22) Filed: Dec. 10, 2003

(51) Int. Cl.
*A61N 1/00* (2006.01)
(52) U.S. Cl. .......................... 607/36; 128/903
(58) Field of Classification Search ............... 607/32, 607/36, 57
See application file for complete search history.

(56) References Cited

U.S. PATENT DOCUMENTS

| | | | | |
|---|---|---|---|---|
| 4,362,153 A | * | 12/1982 | Wilson et al. | 128/202.26 |
| 4,991,582 A | * | 2/1991 | Byers et al. | 607/2 |
| 5,431,695 A | | 7/1995 | Wiklund et al. | 607/36 |
| 5,480,416 A | * | 1/1996 | Garcia et al. | 607/36 |
| 5,782,891 A | | 7/1998 | Hassler et al. | 607/36 |
| 5,861,019 A | * | 1/1999 | Sun et al. | 607/60 |
| 5,913,881 A | * | 6/1999 | Benz et al. | 607/36 |
| 5,925,069 A | * | 7/1999 | Graves et al. | 607/36 |
| 6,009,350 A | | 12/1999 | Renken | 607/36 |
| 6,169,925 B1 | | 1/2001 | Villaseca et al. | 607/32 |
| 6,240,317 B1 | | 5/2001 | Villaseca et al. | 607/60 |
| 6,355,401 B1 | * | 3/2002 | Graves et al. | 430/319 |
| 6,456,256 B1 | * | 9/2002 | Amundson et al. | 343/873 |
| 2002/0123776 A1 | | 9/2002 | Von Arx et al. | 607/60 |
| 2003/0025645 A1 | | 2/2003 | Amundson et al. | 343/873 |
| 2005/0113886 A1 | * | 5/2005 | Fischell et al. | 607/60 |

FOREIGN PATENT DOCUMENTS

| | | |
|---|---|---|
| EP | 0714317 B1 | 9/2002 |
| WO | WO 00/65990 | 9/2000 |
| WO | WO 00/66220 | 9/2000 |

* cited by examiner

*Primary Examiner*—Robert E. Pezzuto
*Assistant Examiner*—Brian T. Gedeon

(57) ABSTRACT

A housing for an implantable medical device comprises a metallic wall including a telemetry window having a thickness that is thinner than the remainder of the housing wall and having an electrical conductivity that is less than that of the remainder of the housing wall. In another embodiment, an implantable medical device casing comprises a metallic wall including a telemetry window received within an aperture defined by said casing wall, the window having an electrical conductivity that is less than that of the remainder of the casing wall. Pursuant to another embodiment, there is provided an implantable medical device incorporating a casing as described above that is hermetically sealed and encloses a transceiver for bidirectional telemetric communication through the telemetry window.

17 Claims, 3 Drawing Sheets

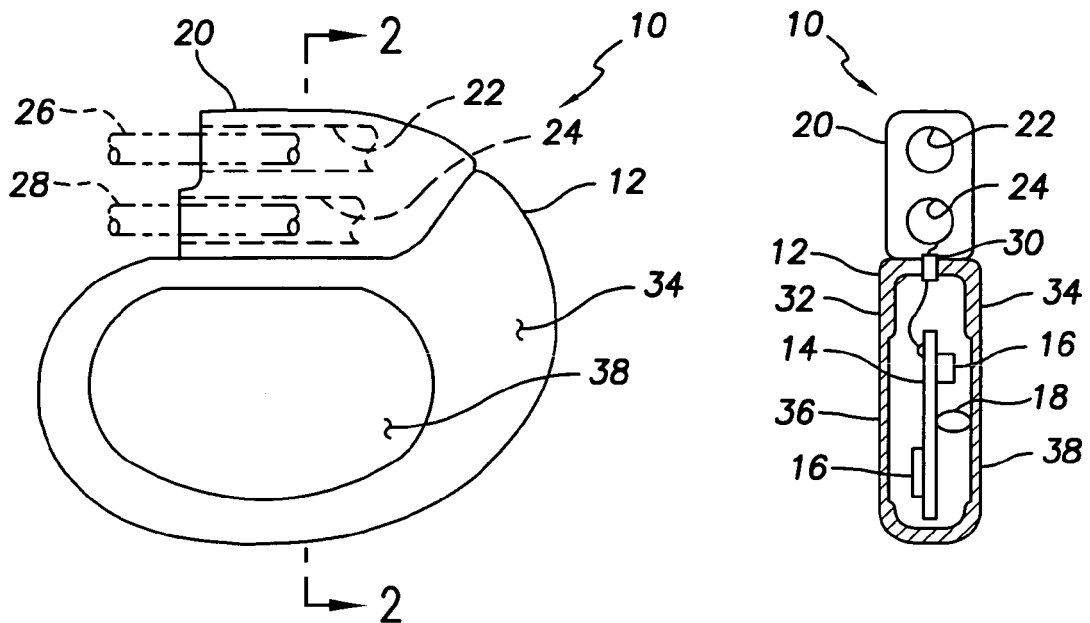
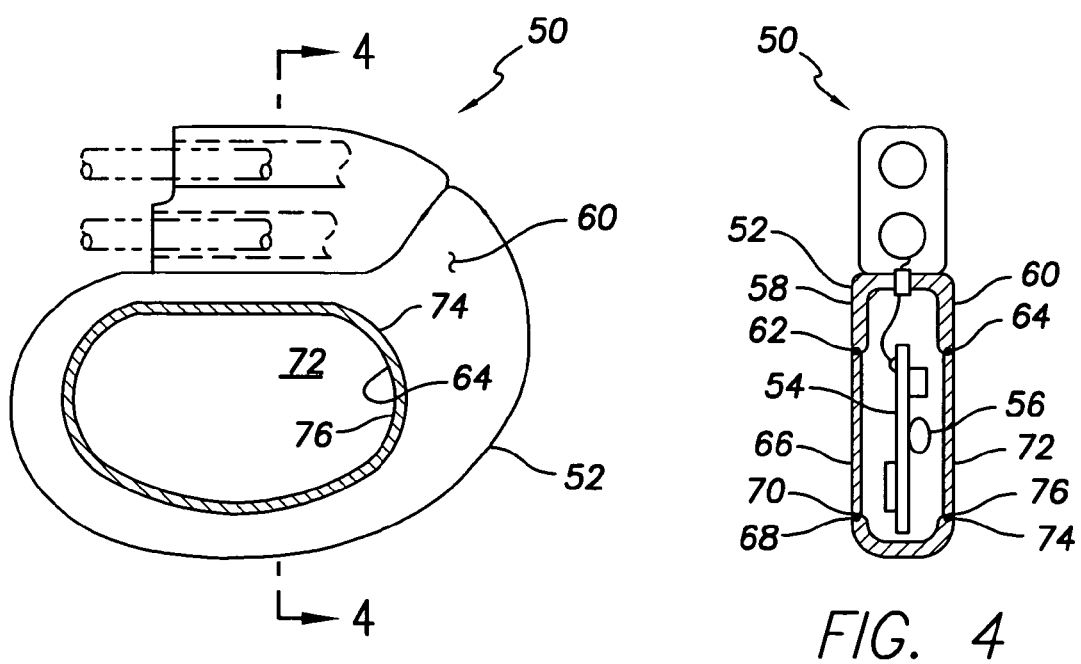

IMPLANTABLE MEDICAL DEVICE HAVING A CASING PROVIDING HIGH-SPEED TELEMETRY

FIELD OF THE INVENTION

The present invention relates generally to implantable medical devices (IMDs) such as cardiac pacemakers or implantable cardioverter defibrillators (ICDs) capable of bidirectional telemetric communication. More particularly, the invention relates to IMD casings constructed to facilitate high-speed telemetric communication.

BACKGROUND

Present day IMDs such as cardiac pacemakers or ICDs incorporate electrical stimulation pulse generators as well as cardiac event sensors that can pace, sense, and/or shock the tissue of the atrium, ventricle, or both the atrium and ventricle of the heart.

Noninvasive telemetry has been developed allowing information such as data and control signals to be bidirectionally communicated, for example, by means of a radio frequency (RF) coupling, between an IMD and an external system. Such an external system, typically comprising a controller, a programmer, and/or a monitor, provides a convenient means through which the operation of the IMD can be controlled and monitored, and through which information sensed by the IMD can be read, interpreted, or otherwise used.

In an RF-coupled system information is transferred from a transmitting antenna to a receiving antenna by way of a radiated carrier signal. The carrier signal is modulated with the data to be transmitted using an appropriate modulation scheme. The modulated carrier induces a voltage in the receiving antenna that tracks the modulated carrier signal. The received signal is then demodulated to recover the transmitted data.

Present day IMDs are enclosed within hermetically sealed casings, typically made of a titanium alloy selected for its high strength, corrosion-resistance, biocompatibility and biostability. An IMD's RF telemetry circuitry comprising, for example, a ferrite core, a wire coil and an RF antenna, is not biocompatible, and therefore must be placed inside the hermetically sealed casing. RF-coupled telemetry through an IMD casing is affected by the properties of the casing, including its material, thickness and geometry. In particular, the rate at which telemetry is possible is largely determined by the electrical conductivity and the thickness of the casing. There has been a significant increase in the complexity of IMDs so that the quantity of information that now must be telemetrically transferred between an IMD and its associated external system has dramatically increased.

Electrical eddy currents great enough to adversely attenuate the radiated RF field and limit the information transfer distance and rate between the IMD and the associated external system can be generated in a metal casing having a high electrical conductivity. A titanium casing, in particular, acts as a low pass filter, attenuating high frequencies so that the carrier frequency cannot be increased above approximately 10–20 kHz without an unacceptable increase in transmitter power. Biocompatible materials having significantly lower electrical conductivities are not available without manufacturability and corrosion problems.

Thus, there continues to be a need for more efficient ways to achieve high-speed telemetric information transfer to and from an IMD. At the same time, it would be advantageous to continue to use a casing material such as titanium that offers the required biostability, biocompatibility, corrosion-resistance, manufacturability and structural strength.

SUMMARY

In accordance with one specific, exemplary embodiment, there is provided a casing for an implantable medical device, the casing comprising a metallic wall including a telemetry window having a substantially uniform thickness that is thinner than the remainder of the casing wall and having an electrical conductivity that is less than that of the remainder of the casing wall. The casing wall, including the telemetry window, may be made of a single metallic material, preferably a metallic material selected from the group consisting of commercially pure titanium and a titanium alloy. Alternatively, the telemetry window and the remainder of the casing wall may be made of different materials, for example, the telemetry window may be made of a titanium alloy and the remainder of the casing wall may be made of commercially pure titanium.

In accordance with another aspect of the implantable medical device, a casing as described above is provided and is hermetically sealed and encloses a transceiver for bidirectional telemetric communication through the telemetry window in the casing wall.

Pursuant to another specific, exemplary embodiment, there is provided a casing for an implantable medical device, the casing comprising a metallic wall including a telemetry window received within an aperture defined by the casing wall, the window having an electrical conductivity that is less than that of the remainder of the casing wall. Preferably, the telemetry window comprises an insert having a peripheral edge bonded to a casing wall edge defining the aperture. In accordance with another aspect of this embodiment, the casing wall and the telemetry window may be made of the same metal, preferably selected from the group consisting of commercially pure titanium and a titanium alloy. Alternatively, the telemetry window and the remainder of the casing wall may be made of different metals, the telemetry window being preferably made of a titanium alloy and the remainder of the casing wall being preferably made of commercially pure titanium.

Pursuant to another illustrative embodiment, there is provided an implantable medical device comprising a casing as described immediately above that is hermetically sealed and encloses a transceiver for bidirectional telemetric communication through the telemetry window.

BRIEF DESCRIPTION OF THE DRAWINGS

The foregoing and other objects, features and advantages of the implantable medical device will be evident to those skilled in the art from the detailed description, below, taken together with the accompanying drawings, in which:

FIG. 1 is a side elevation view of a cardiac pacemaker in accordance with a first specific, exemplary embodiment;

FIG. 2 is an end elevation view, in cross section, of the pacemaker of FIG. 1 as seen along the line 2—2 in FIG. 1;

FIG. 3 is a side elevation view of a cardiac pacemaker in accordance with a second, specific, exemplary embodiment;

FIG. 4 is an end elevation view, in cross section, of the pacemaker of FIG. 3 as seen along the line 3—3 in FIG. 3.

DETAILED DESCRIPTION OF ILLUSTRATIVE EMBODIMENTS

Figure 5:
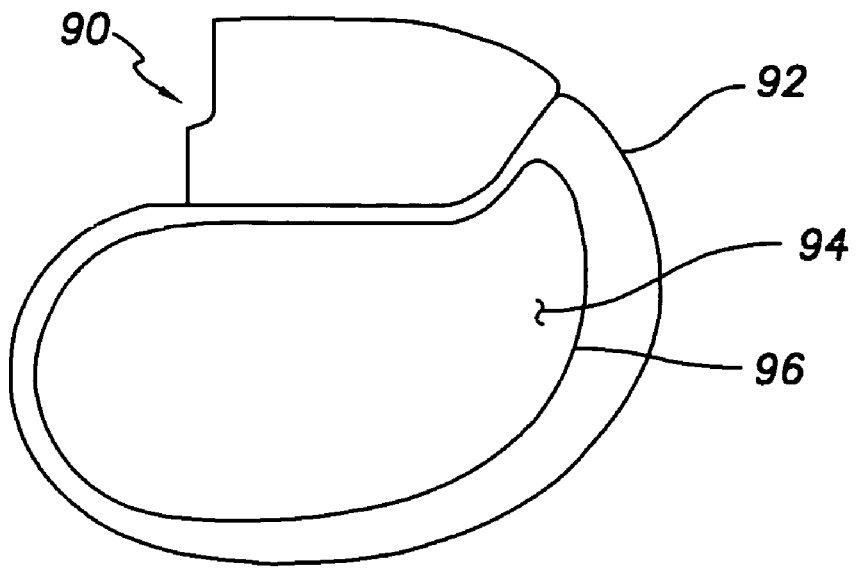
FIGS. 5–8 are side elevation views of cardiac pacemakers pursuant to still further, alternative embodiments of the implantable medical device.

The following description presents preferred embodiments including the best mode contemplated for the implantable medical device. This description is not to be taken in a limiting sense but is made merely for the purpose of describing the general principles of the implantable medical device.

Although the implantable medical device is described in the context of cardiac pacemakers and ICDs, it will be evident that the implantable medical device is equally applicable to a broad range of electronic medical devices implantable in the human body including, but not limited to, devices for the stimulation and/or sensing of the brain, nerves, spinal cord, muscles, bones, glands, or other body organs or tissues.

With reference to FIGS. 1 and 2, there is shown schematically an example of an IMD according to one illustrative embodiment, the IMD being in the form of a cardiac pacemaker 10. The pacemaker 10 comprises a hermetically sealed casing 12 enclosing a circuit board 14 carrying electronic circuitry 16 including a power supply in the form of a battery, an RF transceiver and an RF transceiver antenna 18, typically in the form of a wire-wound coil. The casing 12 is fabricated in conventional fashion of casing halves hermetically joined by brazing, laser welding or the like. Mounted on the casing is a header 20 fabricated of a plastic such as epoxy, or other insulating material. The header 20 includes receptacles 22 and 24 for receiving electrical connector assemblies 26 and 28, respectively, mounted on the proximal end of an electrical lead such as a cardiac pacing lead and/or cardioverting/defibrillating lead. As is well known, such a lead has a distal end carrying one or more electrodes electrically connected to the connector assemblies and adapted to be placed in electrical communication with body tissue to be electrically stimulated and/or whose intrinsic electrical activity is to be sensed. In well-known fashion, terminal contacts on the connector assemblies 26 and 28 of the lead are coupled to the internal electronic circuitry 16 by means of a feedthrough 30.

The hermetically sealed casing 12 is preferably fabricated of commercially pure titanium or a titanium alloy such as Ti-6AI-4V, or other suitable titanium alloy, as are well known to those having ordinary skill in the art. The casing includes parallel sidewalls 32 and 34, each with a wall portion or window 36 and 38, respectively, of a uniform thickness that is thinner than the remainder of the casing wall. By way of example and without limitation, each of the sidewalls 32 and 34 may have a thickness of 0.010 to 0.012 inch while each of the wall portions or windows 36 and 38 may be 0.005 inch thick. In the specific embodiment of FIGS. 1 and 2, each of the windows 36, 38 is formed integrally with the remaining part of the casing wall, that is, as one piece. This may be accomplished by machining each of the sidewalls 32 and 34 to a thin section to define the windows 36 and 38, or by any other suitable process, such as chemical etching and the like.

With reference to FIGS. 3 and 4, there is shown an alternative embodiment of the implantable medical device comprising an IMD in the form of a pacemaker 50 having a hermetically sealed casing 52 enclosing a circuit board 54 carrying electronic circuitry including an RF transceiver antenna coil 56. The casing 52 comprises opposed, parallel, relatively thick sidewalls 58 and 60. Each of the sidewalls 58 and 60 has a cutout or aperture. The aperture in the sidewall 58 is defined by an edge 62; similarly, the aperture in the sidewall 60 is defined by an edge 64. The aperture edges 62 and 64 preferably have substantially identical contours.

Received within the aperture in the sidewall 58 is a window 66 in the form of an insert having an outer peripheral edge 68 configured to correspond to the shape of the aperture edge 62. The insert edge 68 is hermetically bonded to the aperture edge 62 preferably by a continuous weld 70. The weld 70 preferably comprises a butt weld (as shown), but may alternatively comprise a lap weld. Any joinder technique, for example, brazing or laser welding, may be employed. A similar window 72 having an outer edge 74 bonded to the aperture edge 64 preferably by a continuous butt weld 76 may be installed in the aperture formed in the casing sidewall 60. As in the first embodiment, the casing 52 is preferably constructed of a biocompatible, biostable material such as commercially pure titanium or a titanium alloy such as Ti-6AI-4V with sidewalls 0.010 to 0.012 inch thick, while each window or insert 66, 72 may comprise thin sheet commercially pure titanium or titanium alloy, for example, Ti-6AI-4V, 0.005 inch thick. The windows or inserts 66 and 72 may be made of the same material or of a different material than that used for the remainder of the casing wall. Further, the aperture or the window insert or both may have thickened edges to facilitate welding.

Although the windows shown in FIGS. 1–4 have a generally oval periphery, it will be evident that other shapes, including circular, square, rectangular, and so forth, may be utilized. FIG. 5 shows an IMD in the form of a pacemaker 90 comprising a hermetically sealed casing 92 having a high speed telemetry window 94 in one or both of the casing sidewalls. In the embodiment of FIG. 5, the periphery 96 of the window 94 corresponds closely to the shape of the casing. As before, the window 94 may be made integral with the remainder of the casing wall, as one piece, or as an insert fabricated of the same or of a different material used for the remainder of the casing wall and welded in place as already described.

Figure 6:
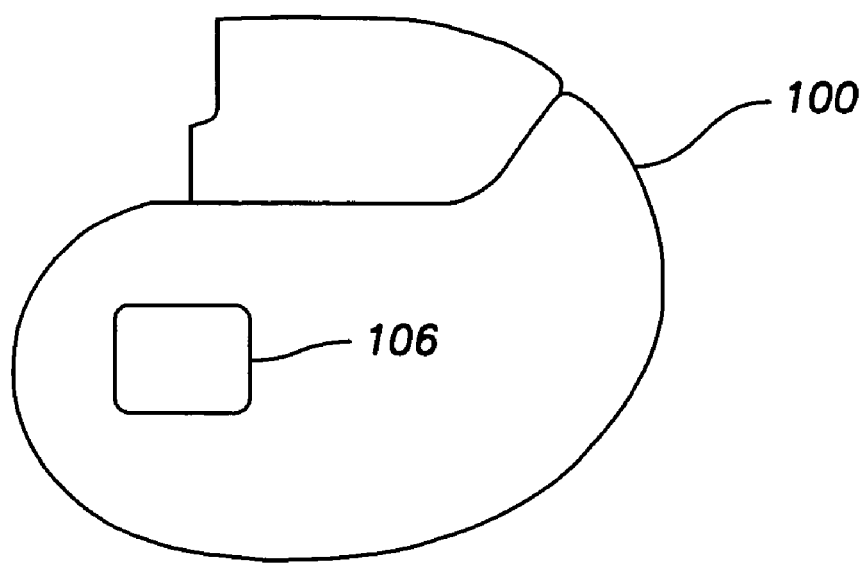
Figure 7:
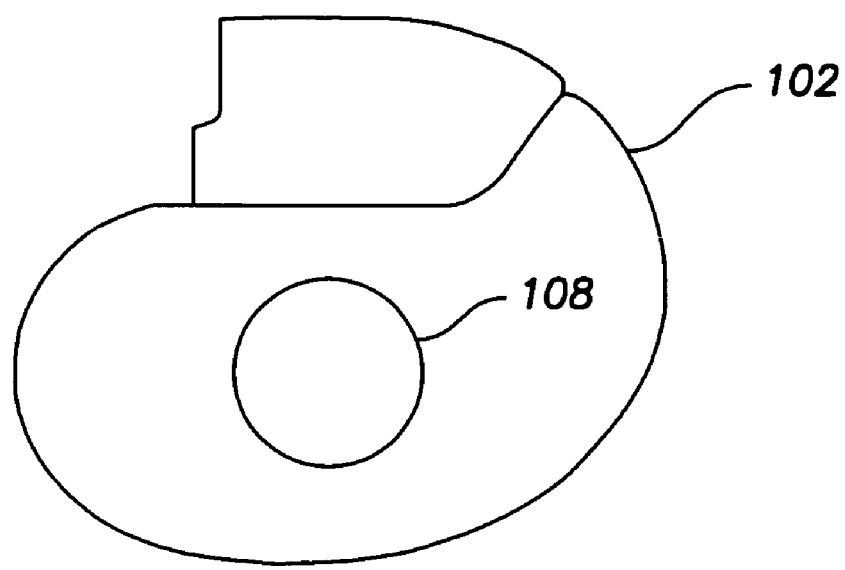
Figure 8:
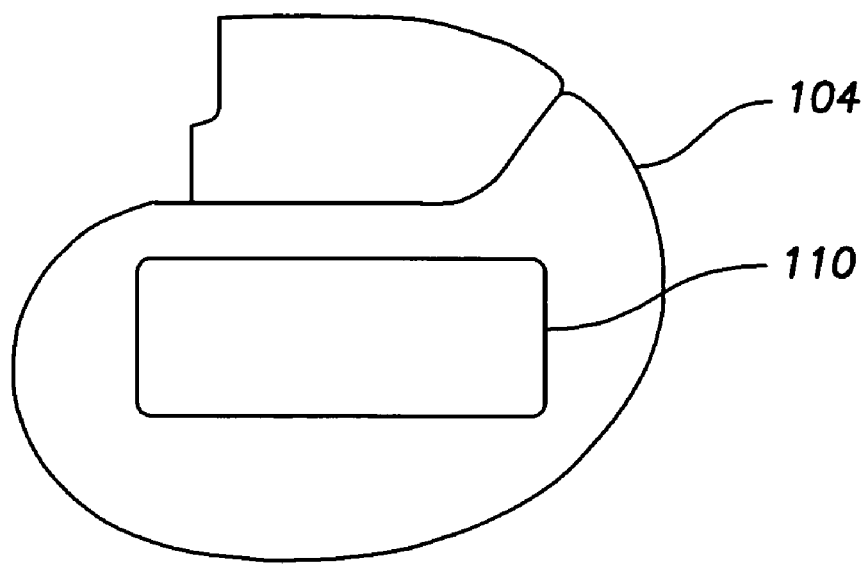

In the embodiments of FIGS. 6, 7 and 8, pacemakers are illustrated having casings 100, 102 and 104 with square, circular and rectangular windows 106, 108 and 110, respectively, either formed integrally with the casing wall or as welded inserts. It will be evident that the sizes of the windows may also be varied; for example, the circular window may have a diameter ranging, for example, from 1.5 cm to 4.0 cm. Larger windows such as those shown in FIGS. 1, 3, 5 and 8 are preferred.

In each of the embodiments described, the wall portion or window has an electrical conductivity that is lower than the remainder of the casing. This is accomplished by making the window thinner than the rest of the casing, or making the window of a material having a lower electrical conductivity, or a combination of both. As a result, eddy current losses generated in the window material are reduced, allowing higher data rate transfer. It will be evident that only one of the casing sidewalls, rather than both sidewalls, may be provided with an aperture and an associated window.

While several illustrative embodiments of the implantable medical device have been shown and described, numerous variations and alternate embodiments will occur to those skilled in the art. Such variations and alternate embodiments are contemplated, and can be made without departing from the spirit and scope of the invention as defined in the appended claims.

What is claimed is:

1. An implantable medical device comprising a housing that defines a telemetry window, wherein the telemetry window comprises a metal and is formed with a substantially uniform thickness that is thinner than the remainder of the housing, the implantable medical device further comprising an antenna disposed with the housing and aligned with the telemetry window.

2. The implantable medical device of claim 1 wherein:
the housing, including the telemetry window, is made of a single metallic material.

3. The implantable medical device of claim 2 wherein:
the single metallic material comprises a metallic material selected from the group consisting of commercially pure titanium and a titanium alloy.

4. The implantable medical device of claim 1 wherein:
the telemetry window and the remainder of the housing are made of different materials.

5. The implantable medical device of claim 4 wherein:
the telemetry window is made of a titanium alloy and the remainder of the housing is made of commercially pure titanium.

6. The implantable medical device of claim 1 wherein:
the telemetry window comprises an insert received within an aperture defined by the housing.

7. The implantable medical device of claim 6 wherein:
the telemetry window insert has a periphery and the aperture has an edge configured to match the periphery.

8. The implantable medical device of claim 1 wherein:
the antenna is part of a transceiver operative to provide bidirectional telemetric communication.

9. An implantable medical device comprising a housing that defines a telemetry window, wherein the telemetry window consists of an electrically conductive material and is formed with an electrical conductivity that is less than that of the remainder of the housing.

10. An implantable medical device comprising a housing that defines a telemetry window, wherein the telemetry window is formed comprising an electrically conductive material with an electrical conductivity that is less than that of the remainder of the housing and the telemetry window comprises an insert received by an aperture in the housing.

11. The implantable medical device of claim 10 wherein:
the insert has a peripheral edge bonded to a casing wall edge defining the aperture.

12. An implantable medical device comprising a housing that defines a telemetry window, wherein the telemetry window is formed comprising an electrically conductive material with an electrical conductivity that is less than that of the remainder of the housing and the telemetry window has a uniform thickness.

13. An implantable medical device comprising a housing that defines a telemetry window, wherein the telemetry window is formed with an electrical conductivity that is less than that of the remainder of the housing and the telemetry window is thinner than the remainder of the housing.

14. The implantable medical device of claim 9 wherein:
the housing and the telemetry window are made of the same metal.

15. The implantable medical device of claim 14 wherein:
the metal is selected from the group consisting of commercially pure titanium and a titanium alloy.

16. An implantable medical device comprising a housing that defines a telemetry window, wherein the telemetry window is formed with an electrical conductivity that is less than that of the remainder of the housing and the telemetry window and the remainder of the housing are made of different metals.

17. The implantable medical device of claim 16 wherein:
the telemetry window is made of a titanium alloy and the remainder of the housing is made of commercially pure titanium.

* * * * *